United States Patent

Nakahara et al.

[11] 4,250,313
[45] Feb. 10, 1981

[54] PROCESS FOR PREPARING 4-PIPERIDONE SPIROKETAL COMPOUNDS

[75] Inventors: Yutaka Nakahara, Iwatsuki; Naohiro Kubota, Ageo; Toshihiro Shibata, Omiya, all of Japan

[73] Assignee: Argus Chemical Corp., Brooklyn, N.Y.

[21] Appl. No.: 117,464

[22] Filed: Feb. 1, 1980

[51] Int. Cl.³ .............................................. C07D 405/04
[52] U.S. Cl. .................................................... 546/19
[58] Field of Search .......................................... 546/19

[56] References Cited

U.S. PATENT DOCUMENTS

| | | |
|---|---|---|
| 3,899,464 | 8/1975 | Murayama et al. ............ 546/19 |
| 4,096,114 | 6/1978 | Minagawa et al. ............ 546/19 |
| 4,105,625 | 8/1978 | Minagawa et al. ............ 546/19 |
| 4,115,476 | 9/1978 | Minagawa et al. ............ 546/19 |
| 4,136,081 | 1/1979 | Minagawa et al. ............ 546/19 |

Primary Examiner—Alan L. Rotman
Assistant Examiner—Robert T. Bond
Attorney, Agent, or Firm—Otto S. Kauder

[57] ABSTRACT

2,2,6,6-Tetramethyl-4-piperidone spiroketal carbinol compound of Formula I

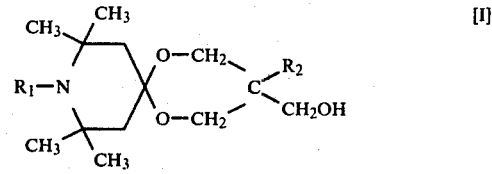

in which $R_1$ represents hydrogen, alkyl of one to ten carbon atoms, or aralkyl of seven to ten carbon atoms, and $R_2$ represents alkyl of one of one to six carbon atoms, is prepared by heating a mixture of a 2,2,6,6-tetramethyl-4-piperidone compound of Formula II

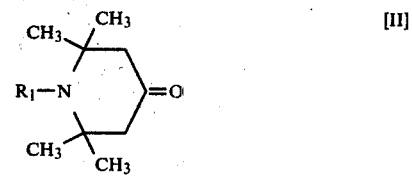

or an acid addition salt thereof, and a 1,3 dioxane compound having the formula III

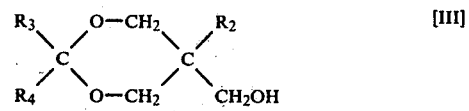

in which $R_3$ and $R_4$ represent $R_1$ or aryl of six to ten carbon atoms or taken together represent alkylene of four to eight carbon atoms, removing $R_3R_4CO$ compound and recovering 2,2,6,6-tetramethyl-4-piperidonespiroketal compound.

14 Claims, No Drawings

PROCESS FOR PREPARING 4-PIPERIDONE SPIROKETAL COMPOUNDS

BACKGROUND OF THE INVENTION

This invention relates to a new process for preparing 4-piperidone spiroketal compounds in excellent yield and purity.

Hindered piperidine alcohol compounds having formula A, which can be named 2,2,6,6-tetramethyl-4-piperidone spiroketal carbinol compounds, or more systematically 9-aza-3-hydroxymethyl-3-alkyl-8,8,10,10-tetramethyl-1,5-dioxaspiro(5,5)undecanes,

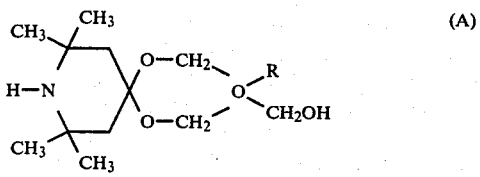

have been disclosed by K. Murayama in U.S. Pat. No. 3,899,464 of Aug. 12, 1975 as stabilizers able to protect synthetic polymers and plastics against the harmful effects of exposure of ultraviolet radiation and heat. Compounds of Formula A have also been disclosed to be valuable synthetic intermediates for the preparation of even better stabilizers by reaction of the compounds at the alcoholic hydroxyl group to form various derivatives. Outstandingly effective stabilizers among these derivatives are certain organic phosphite esters disclosed by M. Minagawa et al in U.S. Pat. No. 4,096,114 of June 20, 1978; hydroxyaliphatic dicarboxylic and tricarboxylic acid esters disclosed by M. Minagawa et al in U.S. Pat. No. 4,105,625 of Aug. 8, 1978; diol bis-carbonate esters disclosed by M. Minagawa et al in U.S. Pat. No. 4,115,476 of Sept. 19, 1978; butane-and butene-tricarboxylic acid esters disclosed by M. Minagawa et al in U.S. Pat. No. 4,116,927 of Sept. 26, 1978; heterocyclic carboxylic acid esters disclosed by M. Minagawa et al in U.S. Pat. No. 4,118,369 of Oct. 3, 1978; and aliphatic tetracarboxylic acid esters disclosed by M. Minagawa et al in U.S. Pat. No. 4,136,081 of Jan. 23, 1979.

Compounds of Formula I have hitherto been prepared as disclosed by Muraymama by the reaction of a tetraalkyl-4-piperidone with a trimethylolalalkane in the presence of an acid catalyst. However, the procedure has required long reaction times and the product was impure; in Murayama's description of this process no product yields are given.

1,3-Dioxane compounds carrying a hydroxymethyl substituent, l.e. Ketal derivatives of trimethylolalkanes, have been known for some time, but no reactions of such compounds with ketones or aldehydes have been reported. The outcome of any such reaction could not have been predicted, since a ketone or aldehyde could attack at the hydroxymethyl group or at the 1,3-dioxane structure or both of these at the same time.

SUMMARY OF THE INVENTION in accordance with this invention, a process for preparing a 2,2,6,6-tetramethyl-4-piperidone spiroketal carbinol compound having the formula I

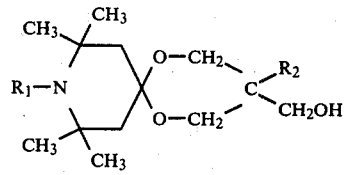

in which $R_1$ represents a hydrogen atom, an alkyl group having one to ten carbon atoms, or an aralkyl group having seven to ten carbons, and $R_2$ represents an alkyl group having from one to six carbon atoms, comprises the steps of heating in the presence of an acid catalyst a mixture of 2,2,6,6-tetramethyl-4-piperidone compound having the formula II

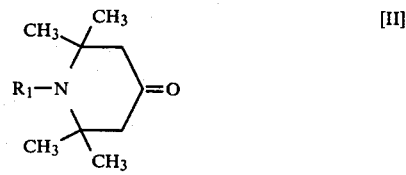

or an acid addition salt hereof, and a 1,3-dioxane compound having the formula III

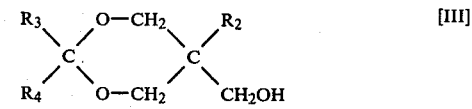

in which each of $R_3$ and $R_4$ independently is an $R_1$ group or an aryl group having six to ten carbon atoms, or taken together $R_3$ and $R_4$ are an alkylene group having four to eight carbon atoms, removing $R_3R_4CO$ compound, and recovering 2,2,6,6-tetramethyl-4-piperidone spiroketal carbinol compound having Formula I from the mixture.

The carbinol compound of Formula I can be obtained according to this invention as the free base, or alternatively as an acid addition salt with any of the acids hydrochloric acid, sulfuric acid, phosphoric acid, hydrobromic acid, p-toluenesulfonic acid, acetic acid, and oxalic acid. Also, the 2,2,6,6-tetramethyl-4-piperidone compound of Formula II can be supplied to the process of this invention as the free base or as an acid addition salt with any of the recited acids.

The process of the invention furnishes the carbinol compound of Formula I in less time and in greater purity as well as better yield than prior art processes.

DESCRIPTION OF THE PREFERRED EMBODIMENTS

In the 2,2,6,6-tetramethyl-4-piperidone spiroketal carbinol compound of Formula I, and in the 1,3-dioxane compound starting material having the formula III the alkyl group $R_2$ can be for example methyl, ethyl, propyl, isopropyl, n-butyl, isobutyl, n-pentyl, 3-methylbutyl, and n-hexyl. The substituent group $R_1$ in the product of Formula I and in the 2,2,6,6-tetramethyl-4-piperidone starting material having Formula II can be a hydrogen atom or any of the alkyl groups $R_2$ as well as n-heptyl, n-octyl, isooctyl, 2-ethylhexyl, nonyl, n-decyl, isodecyl, benzyl, 1-phenethyl, 2-phenethyl, 3,4-dimethylbenzyl, and 4-phenylbutyl. An aryl group $R_3$ or $R_4$ can be, for example, phenyl, tolyl, xylyl, ethylphenyl, cumyl, t-butylphenyl, and naphthyl. An alkylene group in which $R_3$ and $R_4$ are taken together can be for example pentamethylene, tetramethylene, heptamethylene, 2,3-dimethyltetramethylene, 1-methylpentamethylene, and 2,2,4-trimethylpentamethylene.

In the process according to this invention, approximately equimolar proportions of the 1,3-dioxane compound and 2,2,6,6-tetramethyl-4-piperidone compound reactants are used, although an excess of either reactant can be used if desired. The reaction proceeds with generation of carbonyl compound represented by the formula $R_3R_4CO$ in which $R_3$ and $R_4$ are as defined above, and this compound is at some point separated from the desired carbinol compound of formula I. Convenient techniques for accomplishing the removal include partitioning the mixture between water and water-immiscible solvent such as hexane or tolene, whereby a low molecular weight $R_3R_4CO$ is enriched in the water phase and the carbinol compound of Formula I in the solvent phase; crystallization of the carbinol compound of Formula I either as the free base or as an acid addition salt and separation of the crystals by filtration or centrifugation from the mother liquor containing the carbonyl compound or distillation from the reaction mixture after the reaction is finished, or intermittently or continuously while the reaction is proceeding. Distillation represents a particularly preferred technique for removing $R_3R_4CO$. Unlike prior art processes, the reaction in the process of this invention produces no water, and this is believed to be a beneficial feature. Modest amounts of water, however, can be tolerated in the mixture, up to about 2% by weight, without interfering with the process.

The 2,2,6,6-tetramethyl-4-piperidone spiroketal carbinol compound of Formula I, which can also be named according to systematic nomenclature as a 9-aza-3-hydroxymethyl-3-alkyl-8,8,10,10-tetramethyl-1,5-dioxaspiro(5,5)undecane, can be recovered from the mixture in which it is produced as the free base or as an acid addition salt such as the hydrochloride. To recover the free base, the reaction mixture, in wich the carbinol compound of Formula I can be present as an acid addition salt as a result of the use of a 2,2,6,6-tetramethyl-4-piperidone ketal acid addition salt starting material or of an acid catalyst in sufficient quantity, is treated with an excess of a base, which is preferably inorganic and can be used dry or in an aqueous solution. The common inorganic bases are suitable, such as anhydrous ammonia, lime, barium hydroxide and the alkali metal hydroxides and carbonates. The treatment with inorganic base results in the formation of inorganic salt, which can be present as a solid or as an aqueous solution, and an organic phase comprising the desired free base form of the carbinol compound of Formula I and any water-immiscible solvent present. Recovery of the carbinol compound of Formula I is then completed by drying the organic solution and concentrating it, suitably under reduced pressure, until crystallization of the carbinol occurs or to dryness. The crystals can then be collected for packing and shipping or for use in further syntheses by conventional methods.

In the process of this invention the use of an acid catalyst is helpful and is preferred. Suitable acid catalysts have an acid strength indicated by a pK not greater than 3, and include among others hydrochloric acid, sulfuric acid, phosphoric acid, and p-toluenesulfonic acid. The quantity of acid catalyst is suitably from 0.02 to 2 moles per mole of 2,2,6,6-tetramethyl-4-piperidone reactant, preferably from 1.05 mole to 1.25 mole acid catalyst per mole of the piperidone as the free base.

The process of this invention is suitably carried out at any convenient temperature in the range from 20° to 300° C., preferably in the range from 60° to 200° C. An organic solvent can be used to facilitate mixing of the reactants and control of the temperature and rate of reaction. The solvent suitably has a boiling point in the range from 30° to 200° C., and can be a hydrocarbon such as benzene, toluene, xylene, ethylbenzene, cumene, pseudocumene, cymene, hexane, heptane, octane, or cyclohexane; an ether such as diethyl ether or tetrahydrofurane; an amide such as dimethylformamide or dimethylacetamide; a lower aliphatic ketone such as acetone or methyl ethyl ketone, or a lower alcohol such as methanol or ethanol.

The process of this invention can be conveniently carried out at atmospheric pressure, but pressures greater or less than atmospheric can be applied if desired; for example a closed pressure vessel can be used to contain the reaction mixture with diethyl ether as solvent if it is desired to operate above its atmospheric boiling point.

The 1,3-dioxane compound and 2,2,6,6-tetramethyl-4-piperdone starting materials for the process of this invention are known and readily available chemicals, as disclosed, for example, by M. Minagawa in U.S. Pat. No. 4,124,564 of Nov. 7, 1978.

EXAMPLE 1

Preparation of 9-aza-3-hydroxymethyl-3-ethyl-8,8,10,10-tetramethyl-1,5-dioxaspiro(5,5)undecane (compound of Formula I in which $R_1$ is ethyl)

2,2,6,6-Tetramethyl 4-piperidone hydrochloride 20.0 g (0.12 mole), 2,2-dimethyl-5-hydroxymethyl-1,3-dioxane, 17.4 g (0.1 mole), p-toluene sulfonic acid 1.5 g and xylene 200 ml were heated at 120° C. in a stream of nitrogen for 3 hours while removing the generated acetone. Then, 30 ml of 40% aq. KOH was added, and the organic layer was washed with water, dried, and concentrated by evaporation. The product was recrystallized from xylene and 26.0 g of white crystals of mp. 108.5°–109.5° C. was obtained. (yield=94.1%, purity by assay 97%).

The infrared spectrum and elemental analysis of the product corresponded to those of the desired compound.

These results show that the desired compound was successfully produced by the process of this invention in excellent yield and purity.

EXAMPLES 2–7

Various 2,2,6,6-tetramethyl 4-piperidone spiroketal compounds were prepared following the procedure of Example 1. The results were shown in Table 1. Product identity was confirmed by infrared spectrum and elemental analysis.

TABLE I

| EXAMPLE No. | PIPERIDONE (II) Compound | 1,3 DIOXANE (III) Compound | Catalyst | Solvent | Product | m.p. °C. (b.p.) | Yield | Purity |
|---|---|---|---|---|---|---|---|---|
| 2 | 2,2,6,6-tetramethyl-4-piperidone hydrochloride | 3-hydroxymethyl-3-ethyl-1,5-dioxaspiro-[5,5]undecane | HCl gas | xylene | 9-aza-3-hydroxyethyl-3-ethyl-8,8,10,10-tetramethyl-1,5-dioxaspiro[5,5]undecane | 108–109 | 92.4% | 98 |
| 3 | 2,2,6,6-tetramethyl-4-piperidone | 2-propyl-5-ethyl-5-hydroxymethyl-1,3-dioxane | HCl gas | *solvesso 150 | 9-aza-3-hydroxyethyl-3-ethyl-8,8,10,10-tetramethyl-1,5-dioxaspiro[5,5]undecane | 108–110 | 90.5 | 96 |
| 4 | 1,2,2,6,6-pentamethyl-4-piperidone-p-toluene sulfonate | 2-phenyl-2-methyl-5-ethyl-5-hydroxymethyl 1,3-dioxane | p-toluene sulfonic acid | solvesso 150 | 9-aza-3-hydroxymethyl 3-ethyl-8,8,9,10,10-pentamethyl-1,5-dioxa-spiro [5,5]undecane | (152–154/3mmHg) | 91.3 | 97 |
| 5 | 2,2,6,6-tetramethyl-4-piperidone hydrochloride | 2-methyl-2-ethyl-5-hydroxymethyl-1,3-dioxane | p-toluene sulfonic acid | xylene | 9-aza-3-hydroxymethyl-3,8,8,10,10-pentamethyl-1,5-dioxa-spiro[5,5]undecane | 125–126 | 94.7 | 98 |
| 6 | 2,2,6,6-tetramethyl-4-piperidone-p-toluene sulfonate | 2-phenyl-5-methyl-5-hydroxymethyl-1,3-dioxane | p-toluene sulfonic acid | solvesso 150 | 9-aza-3-hydroxymethyl-3,8,8,10,10-pentamethyl-1,5-dioxaspiro[5,5]undecane | 125–126 | 90.7 | 99 |
| 7 | 2,2,6,6-tetramethyl-4-piperidone-p-toluene-sulfonate | 2-methyl-2-isobutyl-5-methyl-5-hydroxymethyl 1,3-dioxane | HCl gas | xylene | 9-aza-3-hydroxymethyl-3,8,8,10,10-pentamethyl-1,5-dioxaspiro[5,5]undecane | 125–126 | 93.8 | 98 |

*solvesso 150: aromatic hydrocarbon solvent (Esso Standard), boiling range 186°–211° C.

These results also show the production of the desired compounds in excellent yield and purity according to this invention.

EXAMPLE 8

Preparation of 9-aza-3-hydroxymethyl-3-ethyl-8,8,10,10-tetramethyl-1,5-dioxaspiro(5,5)undecane hydrochloride.

A mixture of 2,2,6,6-tetramethyl-4-piperidone hydrochloride 19.2 g (0.1 mole), 2,2,-dimethyl-5-ethyl-5-hydroxymethyl-1.3-dioxane 17.4 g (0.1 mole) and Solvesso 150 200 ml were heated at 90° C. for 5 hours while bubbling HCl gas. After cooling, the resulting precipitate was filtered and then recrystallized from benezene-butanol, 8.2 of white crystals of mp. 129°–137° C. was obtained (Yield=92.0%.)

These results show the successful preparation of the desired compound and recovery thereof as the hydrochloride addition salt in excellent yield and purity by the process of this invention.

CONTROL 1

Preparation of 9-aza-3-ethyl-3-hydroxymethyl-8,8,10,10-tetramethyl-1,5-dioxa-spiro 5,5 undecane by prior art process A mixture of 2,2,6,6-tetramethyl-4-piperidone hydrochloride 23.0 g (0.12 mole), trimethylolpropane 13.4 g (0.1 mole), p-toluene sulfonic acid 2 g and xylene 200 ml was reacted at 120° C. in a nitrogen stream for 10 hr. while removing produced water. Then aqueous KOH was added and the product treated as in Example 1. 18.7 g of white crystals were obtained for a yield of 69.0% of theoretical, purity 95%, melting point 106°–108° C.

CONTROL 2

Preparation of 9-aze-3 hydroxymethyl-3-methyl-8,8,10,10-tetramethyl-1,5-dioxaspiro (5,5)undecane by prior art process.

2,2,6,6-Tetramethyl-4-piperidone p-toluenesulfonic acid salt 32.7 g (0.1 mole). trimethylolethane 12.0 g (0.1 mole), p-toluenesulfonic acid 3 g and toluene 200 ml were refluxed for 10 hours while removing produced water.

Potassium hydroxide 40% aqueous solution was added to the mixture and from this point the procedure of Example 1 was followed to obtain 17.5 g (68,1% of theoretical yield) of the free base form of the desired compound as white crystals of melting point 125°–126° C., having=96% assay purity.

These results show that the prior art process affords a lower yield of less pure products than the process of this invention.

We claim:

1. A process for preparing a 2,2,6,6-tetramethyl-4-piperidone spiroketal carbinol compound having the Formula I.

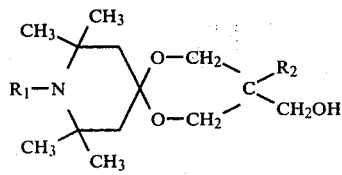

[I]

in which $R_1$ is a hydrogen atom, an alkyl group having one to ten carbon atoms, or an aralkyl group having seven to ten carbons, and $R_2$ is an alkyl group having from one to six carbon atoms, comprising the steps of heating a mixture of 2,2,6,6-tetramethyl-4-piperidone compound having the formula II

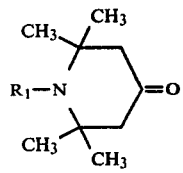

or an acid addition salt thereof, and a 1,3-dioxane compound having the formula III

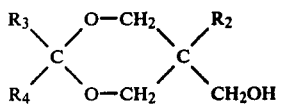

in which each of $R_3$ and $R_4$ independently is an $R_1$ group or an aryl group having six to ten carbon atoms or taken together are an alkylene group having four to eight carbon atoms, removing $R_3R_4CO$ compound, and recovering 2,2,6,6-tetramethyl-4-piperidonespiroketal compound.

2. A process according to claim 1 in which $R_2$ is ethyl.

3. A process according to claim 1 in which $R_2$ is methyl.

4. A process according to claim 1 in which $R_1$ is methyl.

5. A process according to claim 1 in which $R_1$ is hydrogen.

6. A process according to claim 1 in which $R_3$ is an alkyl group having one to four carbon atoms.

7. A process according to claim 1 in which $R_3$ is a hydrogen atom.

8. A process according to claim 1 in which $R_3$ is a phenyl group.

9. A process according to claim 1 in which the reaction temperature is in the range from 60° to 200° C.

10. A process according to claim 1 in which a catalytic quantity of acid catalyst having a pk not exceeding 3 is present in the heated mixture.

11. A process according to claim 10 in which the acid catalyst is one or more of hydrochloric acid, sulfuric acid, phosphoric acid and p-toluenesulfonic acid.

12. A process according to claim 10 in which the quantity of catalyst if from 0.02 to 2 moles per mole of 2,2,6,6-tetramethyl-4-piperidone compound.

13. A process according to claim 1 in which there is used an organic solvent having a boiling point in the range of 30° to 230° C.

14. A process according to claim 1 in which $R_3R_4CO$ compound is removed from the mixture by distillation.

* * * * *